(12) United States Patent
Chen et al.

(10) Patent No.: US 10,463,247 B2
(45) Date of Patent: Nov. 5, 2019

(54) AUTOMATIC THREE-DIMENSIONAL SEGMENTATION METHOD FOR OCT AND DOPPLER OCT ANGIOGRAPHY

(71) Applicants: The Regents of the University of California, Oakland, CA (US); Wenzhou Medical University, Zhejiang (CN)

(72) Inventors: Zhongping Chen, Irvine, CA (US); Lu Fan, Zhejiang (CN); Shenghai Huang, Zhejiang (CN)

(73) Assignee: The Regents of the University of California, Oakland, CA (US)

( * ) Notice: Subject to any disclaimer, the term of this patent is extended or adjusted under 35 U.S.C. 154(b) by 678 days.

(21) Appl. No.: 15/188,839

(22) Filed: Jun. 21, 2016

(65) Prior Publication Data

US 2017/0164825 A1 Jun. 15, 2017

Related U.S. Application Data

(60) Provisional application No. 62/183,072, filed on Jun. 22, 2015, provisional application No. 62/183,601, filed on Jun. 23, 2015.

(51) Int. Cl.
*A61B 3/10* (2006.01)
*A61B 3/00* (2006.01)
*G01N 21/47* (2006.01)

(52) U.S. Cl.
CPC ........... *A61B 3/102* (2013.01); *A61B 3/0025* (2013.01); *G01N 21/47* (2013.01)

(58) Field of Classification Search
None
See application file for complete search history.

(56) References Cited

U.S. PATENT DOCUMENTS

2006/0028648 A1\* 2/2006 Yao ................. G01N 21/274
356/446
2012/0155735 A1\* 6/2012 Friedman ............. A61B 5/0275
382/131

(Continued)

OTHER PUBLICATIONS

Da-Chuan Cheng, Three-Dimensional Expansion of a Dynamic Programming Method for Boundary Detection and Its Application to Sequential Magnetic Resonance Imaging, Apr. 26, 2012, US National Library of Medicine, https://www.ncbi.nlm.nih.gov/pmc/articles/PMC3386679/.\*

(Continued)

*Primary Examiner* — Jason T Yen
(74) *Attorney, Agent, or Firm* — Daniel L. Dawes; Marcus C. Dawes

(57) ABSTRACT

A three-dimensional (three dimensional) segmentation method with intensity-based Doppler variance (IBDV) based on swept-source OCT. The automatic three dimensional segmentation method is used to obtain seven surfaces of intra-retinal layers. The microvascular network of the retina, which is acquired by the IBDV method, can be divided into six layers. The microvascular network of the six individual layers are visualized, and the morphology and contrast images can be improved by using the segmentation method. This method has potential for earlier diagnosis and precise monitoring in retinal vascular diseases. Each tomographic image is composed of eight repeat scans at the same position, which achieves a high time difference to improve the sensitivity of the angiographic method. A subpixel registration algorithm is used to reduce the eye movement. The GPU was used to accelerate the data processing to achieve real-time preview of the acquired data.

16 Claims, 9 Drawing Sheets
(8 of 9 Drawing Sheet(s) Filed in Color)

(56) References Cited

U.S. PATENT DOCUMENTS

| | | | | |
|---|---|---|---|---|
| 2013/0120406 A1* | 5/2013 | Li | | G06T 1/00 |
| | | | | 345/501 |
| 2013/0173750 A1* | 7/2013 | Carnevale | | G06F 19/321 |
| | | | | 709/218 |
| 2013/0258282 A1* | 10/2013 | Goto | | A61B 3/1005 |
| | | | | 351/206 |
| 2013/0258283 A1* | 10/2013 | Goto | | A61B 3/102 |
| | | | | 351/206 |
| 2014/0228681 A1* | 8/2014 | Jia | | G01B 9/02091 |
| | | | | 600/425 |
| 2014/0347627 A1* | 11/2014 | Imamura | | A61B 3/0016 |
| | | | | 351/206 |
| 2015/0094978 A1* | 4/2015 | Hanebuchi | | G01B 9/02069 |
| | | | | 702/106 |
| 2016/0040976 A1* | 2/2016 | Berkeley | | G01N 21/359 |
| | | | | 356/479 |
| 2016/0174830 A1* | 6/2016 | Rubin | | A61B 3/102 |
| | | | | 351/206 |
| 2017/0035286 A1* | 2/2017 | Meyer | | A61B 3/102 |

OTHER PUBLICATIONS

Liu et al., Postprocessing algorithms to minimize fixed pattern artifact and reduce trigger jitter in swept source optical coherence tomography, Apr. 9, 2015, OSA Publishing, https://www.osapublishing.org/DirectPDFAccess/5A4861A1-F198-9664-E0EB2E2B52E63D73_315180/oe-23-8-9824.pdf?da=1&id=315180&seq=0&mobile=no.*

* cited by examiner (a) NFL (b) GCL+IPL (c) INL (h) total retina (i) projection view

AUTOMATIC THREE-DIMENSIONAL SEGMENTATION METHOD FOR OCT AND DOPPLER OCT ANGIOGRAPHY

GOVERNMENT SUPPORT

This invention was made with government support under contract numbers R91 EY-021529, R01HL-125084. P41-E6015890, funded by the National Institutes of Health. The government has certain rights in the invention. This invention was also made with support under contract number 2012YQ12008004, funded by the National Major Equipment Program from the Ministry of Science and Technology in Beijing, China. The government of China also has certain rights in the invention.

RELATED APPLICATIONS

This application is related to provisional patent application, entitled, Automatic Three-Dimensional Segmentation Method for OCT and Doppler OCT Angiography Ser. No. 62/183,072, filed on Jun. 22, 2015, and Ser. No. 62/183,601, filed on Jun. 23, 2015, under 35 USC 119, which are incorporated herein by reference.

BACKGROUND

Field of the Technology

The invention relates to the field of OCT angiography, specifically an apparatus and method for an automatic three-dimensional segmentation method for OCT and Doppler OCT angiography Description of the Prior Art Most retinal diseases are closely related to vasculopathy, such as diabetic retinopathy, retinal vascular occlusive disease, and choroidal neovascularization. Fundus fluorescein angiography (FFA) is widely used in clinical practice and is the gold standard for vascular imaging of the retina and choroid. However, FFA is an invasive procedure with an associated risk of complications which limits clinical applications. In addition, FFA can only provide two-dimensional images of the fundus, and the deeper capillary network may be not visualized well by FFA.

Optical coherence tomography (OCT) is a non-invasive, high-resolution biomedical imaging technology that can provide three-dimensional images of the fundus. Doppler OCT (D-OCT) is a functional extension of OCT which can image not only structure but also blood flow. Compared to the absolute value of flow velocity, the microvascular networks in the retina are also important for diagnosing retinal diseases. A number of methods have been developed to visualize the microvascular networks. A phase-resolved Doppler variance method was first used to map vessels in human skin and within the brain. Since then, it has been used in imaging retinal flow. Yasuno et al. and Wang et al. used a modified Hilbert transform to achieve high resolution images of blood flow. Several extensions of Doppler OCT based on amplitude variance have also demonstrated capabilities of microvascular imaging which are not sensitive to phase noise artifacts, including speckle variance, correlation mapping, split-spectrum amplitude-decorrelation angiography, and intensity based Doppler variance (IBDV). Compared with phase-resolved methods, amplitude variance methods do not depend on phase stability. The IBDV method has been demonstrated in a phase instable situation, and imaging of the human choroidal blood vessel network was also achieved.

Compared with FFA which only shows two-dimensional images of the fundus, OCT can provide three dimensional structure of the fundus. The vascular morphology of intra-retinal layers can be obtained by combining OCT angiography and three dimensional segmentation of intra-retinal layers. It may allow earlier diagnosis and more precise monitoring of some retinal diseases. There are several approaches that have successfully segmented intra-retinal layers in two dimensional images, such as the active contour model, Dijkstra algorithm and dynamic programming. The three dimensional surfaces of the retina can be obtained by applying these two dimensional based algorithms on each image independently. Compared with two dimensional-based methods, three dimensional-based segmentation methods can make full use of the information from neighboring B-scans and help improve the accuracy and robustness of the algorithm. A graph cut-based segmentation method was proposed for simultaneous segmentation of multiple three dimensional surfaces in macula and optic nerve head. However, the minimum cut graph algorithm is computationally expensive which usually requires minutes to complete a three dimensional data segmentation. Cheng et al, proposed a fast three dimensional dynamic programming expansion method for vessel boundary detection on MRI sequences. Efficiency was significantly improved with good robustness, and this method can be used in retinal boundary detection.

BRIEF SUMMARY

In the invention, we combine the three dimensional dynamic programming method with intensity-based Doppler variance based on swept source OCT (SS-OCT). The microvascular morphology of intra-retinal layers are visualized in a normal subject by using this method. Imaging of the microvascular network with three dimensional structure of the retina has potential for earlier diagnosis and precise monitoring in retinal vascular diseases.

The illustrated embodiment of the invention includes a three-dimensional segmentation method with a Doppler variance method to visualize the microvascular network of the individual layers in retina. The microvascular network is obtained in a non-invasive way. The morphology of the microvascular network for individual layers can provide the clinicians valuable information for earlier diagnosis and precise monitoring in retinal vascular diseases.

The three-dimensional structure of retina is obtained by using a swept source optical coherence tomography (OCT) system. Each tomographic image is composed of eight repeat scans at the same position, which achieves a high time difference to improve the sensitivity of the angiographic method. A subpixel registration algorithm is used to reduce the eye movement. A graphics processing unit (GPU) was used to accelerate the data processing to achieve real-time preview of the acquired data.

In an alternative embodiment, the three dimensional structure can also be acquired by using a spectral domain OCT system.

The Doppler variance method is used to visualize the retinal vasculature. A high time difference is achieved by repeated scans. A threshold based on the histogram analysis of the averaged intensity images is used to remove the noise. The morphology of the microvascular in macula and optic disc area is valuable for clinicians to diagnosis retinal diseases.

A three dimensional expansion of a dynamic programming method is used for automated boundary detection. The boundaries are obtained by searching for an optimal path. The surfaces of the seven intra-retinal layers were detected by the automatic algorithm. Compared with the two dimensional image segmentation algorithm in retina, the three dimensional expansion dynamic programming method can use the information from neighboring B-scans to improve the accuracy and robustness of the algorithm. The efficiency is high with good robustness.

The microvascular network of the intra-retinal layers can be obtained by combining the three dimensional automatic segmentation method with intensity-based Doppler variance method. Segmentation of the individual layers can help to separate vessels which may sheltered by upper vessels and help to improve the quality of an OCT angiography image.

The illustrated embodiments of the invention are not limited to retinal vessels. It can also be applied in other tissues, such as iris, conjunctiva vessels, to improve the contrast of the vessel images.

The illustrated embodiment of the invention, which can obtain the en face projection view of the microvascular network for six intra-retinal layers in eyes, will obtain an earlier diagnosis and precise monitoring in retinal vascular diseases. The contrast of the microvascular images can also be improved by using the illustrated embodiment of the invention.

In summary, the illustrated embodiments include a method for microvascular imaging include the steps of: scanning a target tissue having a microvascular network using intensity-based Doppler variance optical coherence tomography (IBDV OCT) with a swept source to obtain three dimensional optical coherence tomography (OCT) data of the target tissue; preprocessing the OCT data; determining boundaries of tissue layers within the target tissue by using a three dimensional expansion of a dynamic programming algorithm, the boundaries being determined by searching for an optimal path: and displaying selected microvascular image views of the three dimensional data of the target tissue with the determined boundaries of the tissue layers within the target tissue.

The step of scanning a target tissue having a microvascular network using intensity-based Doppler variance optical coherence tomography with a swept source to obtain three dimensional OCT data of the target tissue includes the step of making repeated scans at each position to achieve maximized time differences to improve sensitivity.

The step of preprocessing the OCT data includes the step of preprocessing the OCT data with a subpixel registration algorithm to reduce the eye movement.

The step of preprocessing the OCT data includes the step of preprocessing the OCT data with a graphics processing unit (GPU) to accelerate data processing to achieve real-time preview of the acquired OCT data.

The step of preprocessing the OCT data with a graphics processing unit (GPU) to accelerate data processing to achieve real-time preview of the acquired OCT data includes the step of performing fixed pattern noise removal, spectral shaping zero-padding and numerical dispersion compensation accelerated by GPU processing.

The step of preprocessing the OCT data includes the step of preprocessing the OCT data with a threshold based on the histogram analysis of the averaged intensity images to remove noise.

The target tissue is the retina and the step of determining boundaries of tissue layers within the target tissue by using a three dimensional expansion of a dynamic programming algorithm includes the step of determining an initial location of the ILM and RPE layers from an A-scan profile.

The step of determining an initial location of the ILM and RPE layers from an A-scan profile then further includes the step of smoothing the ILM/RPE layers using a polynomial method, limiting a search area for the ILM layer based on the initial ILM boundary and refining the location of the layer by finding the optimal path in the limited search area to determine retina location.

The step of determining boundaries of tissue layers within the target tissue by using a three dimensional expansion of a dynamic programming algorithm includes the step of determining limited search areas for other boundaries of tissue layer based on the characteristics of retinal structure by first determining the outer plexiform layer/outer nuclear layer (OPL/ONL layer) boundary and photoreceptor inner segment layer/outer segment (IS/OS) layer boundary by using an intensity transition along a z axis direction between adjacent layers being in opposite directions, surfaces of the ILM layer, nerve fiber layer/retinal ganglion layer (NFL/GCL) boundary, inner plexiform layer/inner nuclear layer (IPL/INL) boundary, INL/OPL boundary, OPL/ONL boundary, IS/OS boundary, and RPE/Choroid boundary being determined by limiting a search region corresponding to the layer based on previous layers.

The step of determining boundaries of tissue layers within the target tissue by using a three dimensional expansion of a dynamic programming algorithm further includes the step of applying a two dimensional average filter to the segmentation results to get smooth surfaces for the corresponding boundaries.

The step of displaying selected microvascular image views of the three dimensional data of the target tissue with the determined boundaries of the tissue layers within the target tissue includes the step of combining volumetric microvascular signal of the retina with three dimensional surface data of the boundaries by segmenting IBDV OCT data into different layers.

The method further includes the step of producing an en face projection view of the microvascular network for intra-retinal layers by using maximum intensity projection (MIP).

The step of determining boundaries of tissue layers within the target tissue by using a three dimensional expansion of a dynamic programming algorithm, the boundaries being determined by searching for an optimal path, includes the step of transforming detection of the boundaries into an optimization problem that searches for an optimal path across the boundaries.

The step of transforming detection of the boundaries into an optimization problem that searches for an optimal path across the boundaries includes the step of: treating each pixel as a node in a graph with links connecting the nodes; assigning weights to the links based on the intensity of the pixels; defining a virtual start node which connects to nodes in a first column in a two dimensional image grid with the corresponding weights of the links connected to the start node being assigned to zero; defining a virtual end node which connects to nodes in a last column of the two dimensional image grid; defining a boundary by searching for a minimum cost of a path from the start node to end node; and defining the boundary surfaces by sequentially searching in a fast scan plane and then in a slow scan plane for three dimensional expansion.

The step of defining a boundary by searching for a minimum cost of a path from the start node to end node includes the step of: using an iterative cost function in two directions in a volumetric image $R(x, y, z)$ of size $X \times Y \times Z$; where the volumetric image $R(x, y, z)$ is an intensity gradient image along a vertical direction which is obtained by a dark-to-light or light-to-dark intensity transition; where the X and Y are the numbers of fast scan and slow scan respectively, and Z denotes the depth; where the iterative cost function is given by $$C_1(x, y, z) = \min_{-d_1 \leq i \leq d_1} \{C_1(x+i, y-1, z) + \alpha_1|i| + w(x+i, x)\} \quad (2)$$

$$C_2(x, y, z) = \min_{-d_2 \leq j \leq d_2} \{C_2(x-1, y+j, z) + \alpha_2|j|\} + C_1(x, y, z)$$

for $1<x\leq X$ and $1<y\leq Y$; where $C_1$ and $C_2$ are the accumulation costs in the x–z plane and the y–z plane, respectively; where in initialization of $C_1$ and $C_2$ are assigned by R(x, y, z); where the parameters $d_1$ and $d_2$ constrain a searching range used to control the smoothness of boundary surfaces; where the parameters $\alpha_1$ and $\alpha_2$ are used to control the smoothness of the surfaces; where w(x+i, x) denotes the weights from node (x+i, y−1, z) to node (x, y, z) and the weights are calculated as follows:

$$w(x+i,x)=2-r(x+i,y-1,z)-r(x,y,z)+w_{min} \quad (3)$$

where r(x, y, z) is the gradient value of the node (x, y, z) which is normalized to values between 0 and 1; where the $w_{min}$ is a minimum weight for system stabilization. For retinal segmentation, the parameters $\alpha_1$ and $\alpha_2$ are set to zero.

The step of determining boundaries of tissue layers within the target tissue by using a three dimensional expansion of a dynamic programming algorithm, the boundaries being determined by searching for an optimal path includes the step of automatically determining boundaries of tissue layers within the target tissue by using a three dimensional expansion of a dynamic programming algorithm, the boundaries being determined by searching for an optimal path.

The scope of the embodiments of the invention also include a method for imaging a plurality of layer segments in retinal tissue characterized by a plurality of surfaces of corresponding intra-retinal layers including: imaging the plurality of layer segments in retinal tissue using intensity-based Doppler variance (IBDV) OCT based on swept-source OCT; and using three dimensional segmentation of the intensity-based Doppler variance (IBDV) OCT data image of the plurality of layer segments in retinal tissue to determine a three dimensional shape of each of the plurality of surfaces of intra-retinal layers.

The step of imaging the plurality of layer segments in retinal tissue using intensity-based Doppler variance (IBDV) OCT based on swept-source OCT includes the step of obtaining complex valued OCT image data using a three dimensional raster scan and preprocessing the OCT image data by using a plurality of sequential scans at each position, by averaging intensity image data, by using a threshold based on histogram analysis of the averaged intensity image data to remove the noise, by using a subpixel registration algorithm to reduce eye movement; and by using GPU data processing to achieve real-time preview of the acquired data.

The step of using three dimensional segmentation of the intensity-based Doppler variance (IBDV) OCT data image of the plurality of layer segments in retinal tissue to determine a three dimensional shape of each of the plurality of surfaces of intra-retinal layers includes the step of using three dimensional expansion of a dynamic programming algorithm for automated boundary detection, where corresponding boundaries of the plurality of surfaces of intra-retinal layers are obtained by searching for an optimal path across the boundaries.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3b is a cross sectional view of the retina marked by blue fine seen in FIG. 3a.

FIG. 3c is a cross sectional view of the retina marked by green line seen in FIG. 3a.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

We have invented a functional optical imaging system for diagnosis of eye diseases. This system combines an automatic three-dimensional segmentation method with a Doppler variance method based on Fourier domain optical coherence tomography (OCT) to provide an earlier diagnosis and precise monitoring in retinal vascular diseases.

Figure 5:
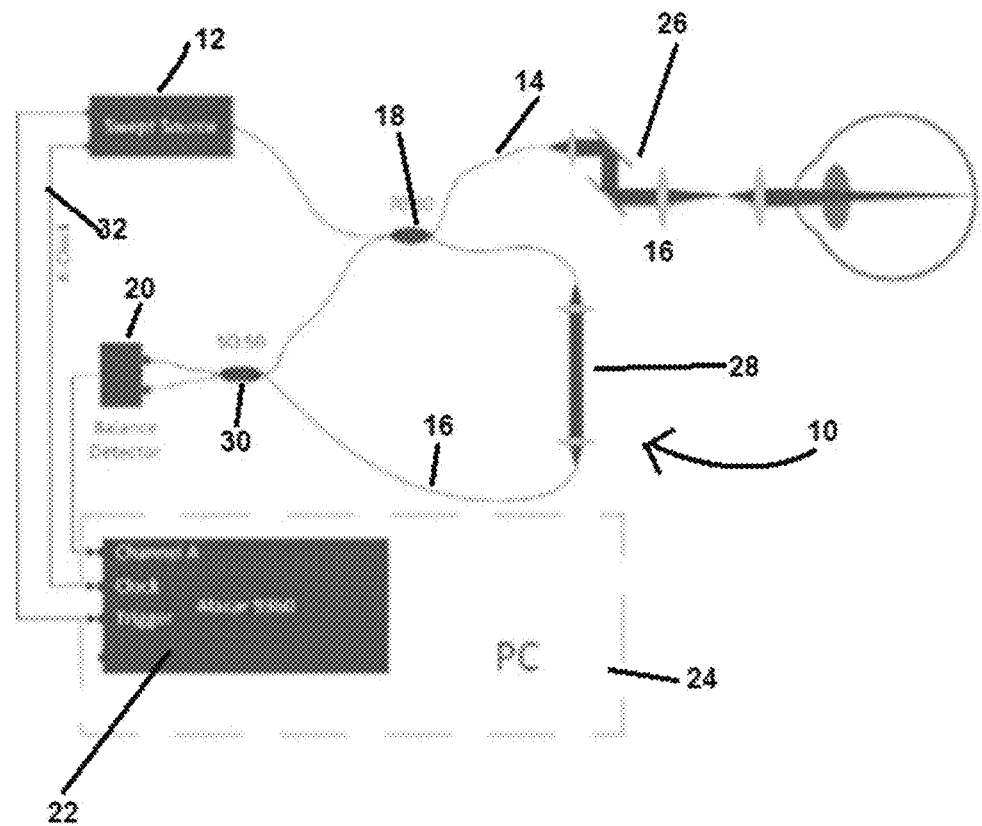
FIG. 5 is a schematic diagram of a 1050 nm swept source OCT system used to perform the current invention.

In the illustrated embodiment, a conventional 1050 nm swept-source OCT system 10 was used to acquire the three dimensional data of the fundus as diagrammatically shown in FIG. 5. A commercially available swept-source laser 12 (for example as are available from Axsun Technologies Inc., Billerica, Mass., USA) with a center wavelength of 1050 nm and 100 nm tuning range was used. The configuration of the system 10 is conventional and has already been described in previous publications, including "Ultrahigh speed 1050 nm swept source/Fourier domain OCT retinal and anterior segment imaging at 100,000 to 400,000 axial scans per second," (Potsaid et al., Opt Express 18(19), 20029-20048 (2010)).

The light from the laser source 12 is split into reference arm 16 and sample arm 14 by a 2×2 fiber coupler 18. A Mach-Zehnder type interferometer setup may be used, and 90% of the laser light power is sent to the sample arm 14 and 10% of the light to the reference arm 16. The sample arm 14 includes galvo scanners and related optics, generally denoted by reference numeral 26. The reference arm 16 includes optics and a dispersion matching glass and water cell, generally denoted by reference numeral 28. The interference signal which returns from the reference arm 16 and sample arm 14 through a 2×2 coupler 30 is detected by a balanced detector 20. The interference signal is digitized by a high speed data acquisition board 22 within computer 24. The acquisition rate of the system is 100 kHz.

The axial resolution was 6.4 µm, and the image range was 3.0 mm at the retina (n=1.38). The interference signal was digitized by a 12 bit 500 MHz data acquisition board 22, (ATS9350 Alazar Technologies Inc., Pointe-Claire, QC, Canada), and the signal acquisition was triggered by an optical clock signal, Clock K, generated by the Axsun laser. The signal to noise ratio (SNR) of the system 10 was 95 dB with 1.8 mW of sample arm power and 100 kHz acquisition rate. A 3 dB sensitivity roll-off from 0.1 mm imaging depth to 1.5 mm imaging depth was measured.

Three right eyes (2 normal subjects and 1 high myopia patient) were used to demonstrate the feasibility of the method under the protocols approved by the Institutional Review Board (IRB) Each set of three dimensional measurements was composed of 200 slices of 400 A-lines over an area of 2.5 mm by 2.5 mm. Each slice was composed of eight sequential B-scans at the same position, which can achieve a high time difference (T) to improve the sensitivity of the IBDV method. The total acquisition time of a three dimensional volumetric data was approximately 6.8 seconds including the flyback time. The subject was asked to fixate on an internal target during the data acquisition.

Custom-built OCT data acquisition and processing software was developed with Microsoft. Visual C++ 2012. In order to achieve real-time preview of the acquired data, a GPU-accelerated computing technique was used with NVIDIA Corporation's compute unified device architecture (CUDA, 6.5) toolkit. The swept source optical coherent tomographic (SS-OCT) preprocessing, including fixed pattern noise removal, spectral shaping, zero-padding and numerical dispersion compensation, was accelerated by GPU processing.

Figure 1:
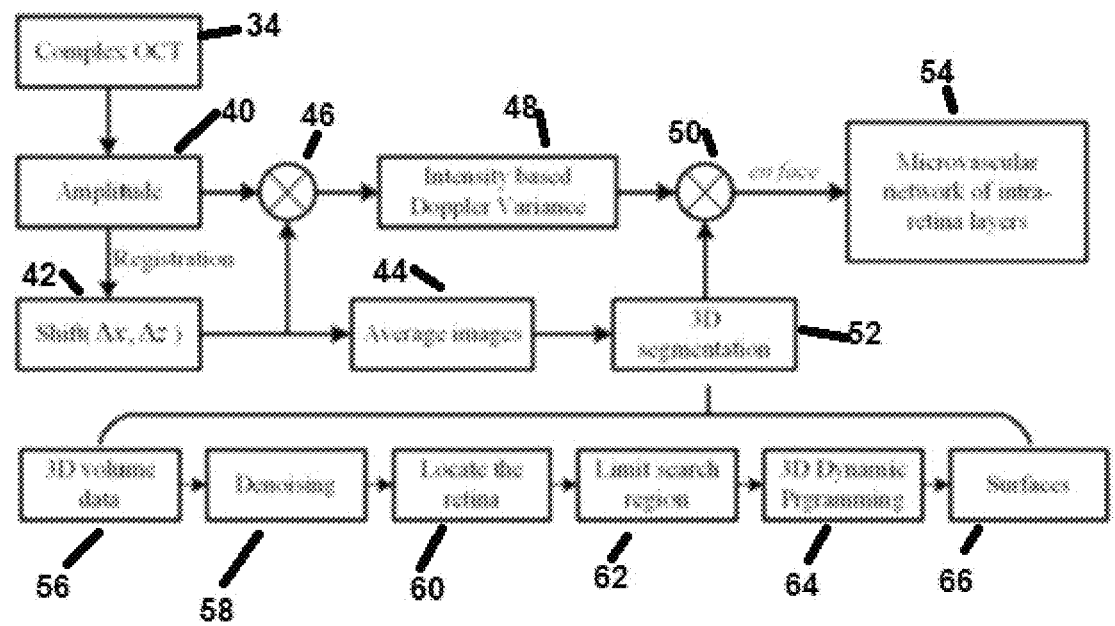
FIG. 1 is a flow diagram of the IBDV imaging process with three dimensional segmentation of the current invention.

FIG. 1 is a flow diagram of the IBDV imaging process with three dimensional segmentation. FIG. 1 specifically shows the flow diagram of the IBDV method combined with three dimensional segmentation after obtaining the complex valued OCT image data by preprocessing the interference signal. OCT data is first collected with an OCT system at step 34, for example, a spectral domain OCT, or a swept source OCT system 10. Raster scan patterning is then used to acquire three dimensional data of the retina. Each slice is composed of eight sequential B-scans at the same position, which can achieve a high time difference (T) to improve the sensitivity of the intensity-based Doppler variance (IBDV) method.

The intensity-based Doppler variance method was used to visualize the retinal vasculature. The time difference (T) was increased by using an inter-frame method. Although the motion artifacts were significantly attenuated because of the improvement of acquisition speed, the motion between B-scans still cannot be ignored, especially the axis motion. A subpixel registration algorithm was used to align sequential B-scans in both the fast transverse direction, x, and axial direction, z. The variance value ($\sigma^2$) between sequential B-scans in the same position is given by, $$\sigma^2 = \frac{1}{T^2}\left[1 - \frac{\sum_{m=1}^{M}\sum_{n=1}^{N-1}(|A_{n,m}||A_{n+1,m}|)}{\sum_{m=1}^{M}\sum_{n=1}^{N-1}\frac{1}{2}(|A_{n,m}|^2 + |A_{n+1,m}|^2)}\right] \quad (1)$$

where M is the number of the depth points that are averaged and N is the number of the B-scans at the same position. The signal-to-noise ratio (SNR) can be increased by choosing a larger Z and N. In this application, the M is set at two and the N is set at eight, $A_{n,m}$ denotes the amplitude value which is extracted from complex valued OCT data. Finally, a threshold based on the histogram analysis of the averaged intensity images is used to remove the noise.

In order to get the vascular morphology of the intra-retinal layers, the boundaries of each layer are required. We used a three dimensional expansion of the dynamic programming method for automated boundaries detection. The basic idea of the method is to transform the boundary detection problem into an optimization problem that searches for an optimal path. In two dimensional images, each pixel is treated as a node in the graph, and the links connecting the nodes are called edges. The values of the links are assigned based on the intensity of the pixels. The start node is a virtual node which connects to the nodes in the first column in the image and the weights are assigned to zero. Correspondingly, the end node is also a virtual node which connects to the nodes in the last column. The boundaries can be found by searching for the minimum cost of the path from the start node to end node. For three dimensional expansion, the surfaces of the layers were achieved by performing the search process in the fast scan plane and slow scan plane sequentially. The dynamic programming provides an efficient optimization method to find the minimum cost of the surface.

Consider a volumetric image R(x, y, z) of size X×Y×Z, where the X and Y are the numbers of fast scan and slow scan respectively, and Z denotes the depth. The iterative cost function in two directions is given by $$C_1(x, y, z) = \min_{-d_1 \leq i \leq d_1} \{C_1(x+i, y-1, z) + \alpha_1|i| + w(x+i, x)\} \quad (2)$$

$$C_2(x, y, z) = \min_{-d_2 \leq j \leq d_2} \{C_2(x-1, y+j, z) + \alpha_2|j|\} + C_1(x, y, z)$$

for $1 < x \leq X$ and $1 < y \leq Y$, where $C_1$ and $C_2$ are the accumulation costs in the x–z plane and the y–z plane, respectively. The initialization of $C_1$ and $C_2$ are assigned by R(x, y, z). The parameters $d_1$ and $d_2$ constrain the searching range which can be used to control the smoothness of the surfaces. The parameters $\alpha_1$ and $\alpha_2$ are also used to control the smoothness of the surfaces. For retinal segmentation, the parameters $\alpha_1$ and $\alpha_2$ are set to zero. The volumetric image R(x, y, z) is the intensity gradient image along the vertical direction which is obtained by a dark-to-light or light-to-dark intensity transition. w(x+i, x) denotes the weights from node (x+i, y−1, z) to node (x, y, z) and the weights can be calculated as follows:

$$w(x+i,x)=2-r(x+i,y-1,z)-r(x,y,z)+w_{min} \quad (3)$$

where r(x, y, z) is the gradient value of the node (x, y, z) which is normalized to values between 0 and 1. The $w_{min}$ is the minimum weight for system stabilization, which is set at $1 \times 10^{-5}$.

Returning to the flow diagram of FIG. 1, the figure outlines the core steps of the three dimensional segmentation method for the retina. The amplitude of the image pixels is determined at step 40 in a B scan. Sequential B-scans are registered at step 42 to minimize motion artifacts. The averaged images were obtained from eight consecutive B-scans after registration of the pixels at step 44. Before segmentation at step 52, a three dimensional median filter is applied to the volumetric data using a window size of 5×3×5 voxels in step 44. Segmentation of the data into various tissue layers of the retina is performed at step 52 using the methodology described below. The IBDV OCT data set is generated at step 48 and combined with the segmentation data determining the retinal boundary structures as described below. The volumetric IBDV OCT data is then produced in each tissue segment in an en face projection of the microvascular network in step 54. The segmentation step 52 is further depicted in the bracketed steps 56-66 shown on the bottom portion of FIG. 1. The three dimensional OCT intensity volume data set is produced at step 56 and noise is removed at step 58 using fixed pattern noise removal. The retina is initially located with a rudimentary boundary determined at step 60. Based on this initial location of the retina, a reduced search area is first defined for determining the boundary of the ILM layer at step 62. Using the reduced search area, a refined location of the ILM layer is determined at step 64. The remaining 7 layers of the retina are dynamically determined in turn in a daisy-chain fashion by repeatedly performing step 62, which defines almited search area for the specific layer, and then step 64, which refines the location of the layer. Having determined the boundaries of the retina segments, the boundary surfaces between the retinal segments are digitally smoothed for final definition at step 66.

The initial location of the retina is determined by the inner limiting membrane (ILM) layer and retinal pigment epithelium (RPE) layer. The inner limiting membrane is the boundary between the retina and the vitreous body, formed by astrocytes and the end feet of Müller cells. It is separated from the vitreous humor by a basal lamina. The pigmented layer of retina or retinal pigment epithelium (RPE) is the pigmented cell layer ust outside the neurosensory retina that nourishes retinal visual cells, and is firmly attached to the underlying choroid and overlying retinal visual cells.

Figure 2A:
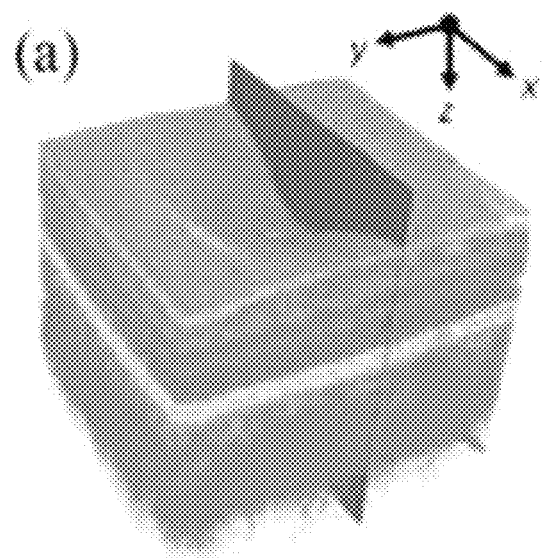
FIG. 2a is a three dimensional volume rendering of the retina centered on the macular fovea formed by using a three dimensional expansion of the dynamic programming method of the current invention.
Figure 2B:
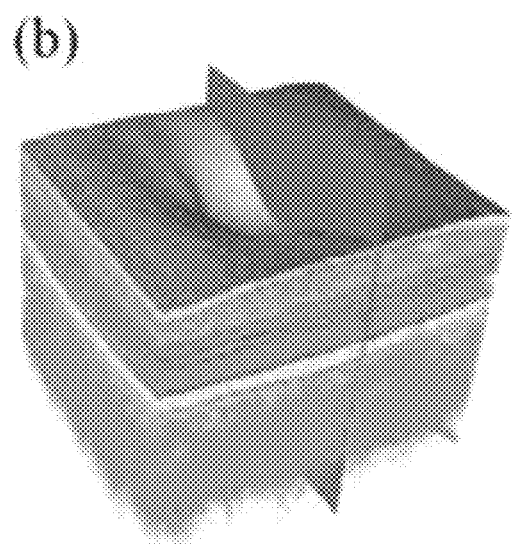
FIG. 2b is a three dimensional rendering of the seven segmented surfaces from ILM layer to RPE/Choroid boundary formed by using a three dimensional expansion of the dynamic programming method of the current invention.
Figure 2C:
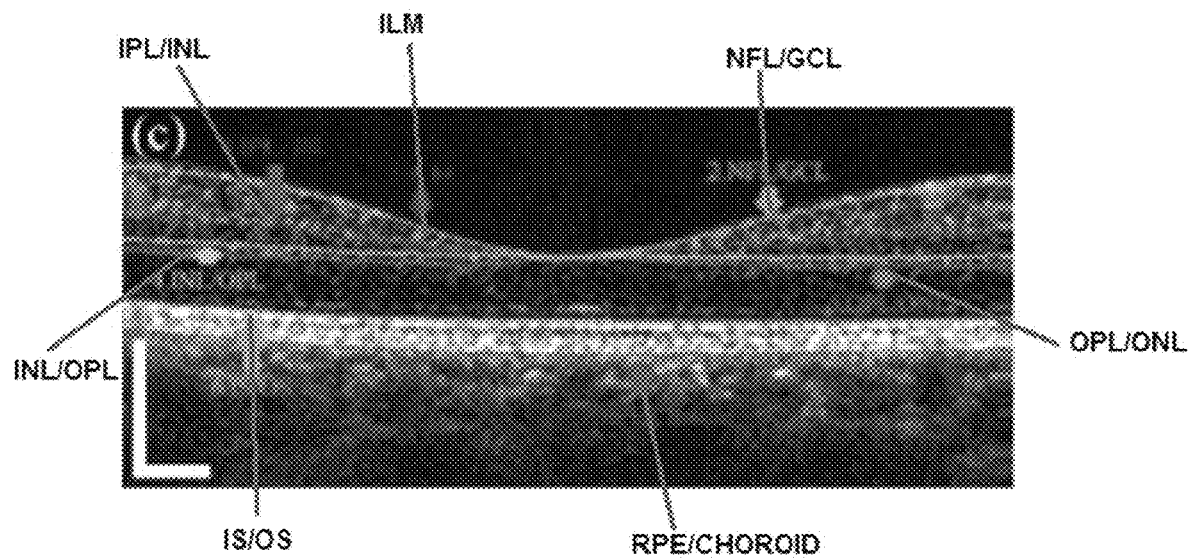
FIG. 2c is a cross sectional image of the corresponding overlaid images with segmented boundaries indicated by the planes in FIGS. 2a and 2b. The segmented boundaries from the inner portion of the retina to the outer portion of the retina are: 1. ILM; 2. NFL/GCL; 3. IPL/INL; 4. INL/OPL; 5. OPL/ONL; 6. IS/OS; and 7. RPE/Choroid.

The ILM layer is defined as the first high reflective increase from the inner side of the retina, and the RPE layer can be determined as the highest peak after the ILM layer. So the initial location of the ILM and RPE layers can be determined from the A-scan profile. After being smoothed by using polynomial method, the search area for the ILM layer can be reduced based on the initial rudimentary ILM boundary. Finally, the ILM layer is refined by finding, the optimal path in a limited region. After obtaining the location of the retina, the limited search region can be determined based on the characteristics of retinal structure. The outer plexiform layer/outer nuclear layer (OPL/ONL layer) and photoreceptor inner segment/outer segment (IS/OS) layers are the most obvious layers besides the ILM layer, and the intensity transition along the axis direction between two layers are in opposite directions. So these two layers can be determined first. The other surfaces can also be obtained by limiting the search region based on previous layers. A two dimensional average filter is applied to the segmentation results to get smooth surfaces. Finally, the surfaces of ILM, nerve fiber layer/retinal ganglion layer (NFL/GCL), inner plexiform layer/inner nuclear layer (IPL/INL), INL/OPL, OPL/ONL, IS/OS, RPE/Choroid (as seen in FIG. 2c) are detected by the automatic algorithm.

Combined with the three dimensional surfaces data, the volumetric microvascular signal of the retina can be segmented into different layers from the IBDV OCT data set. The en face projection view of the microvascular network for intra-retinal layers is produced by using the maximum intensity projection (MIP) method.

The three dimensional OCT data of the retina from a normal subject was collected to test the feasibility of the method. The seven surfaces of the intra-retinal layers were segmented automatically by the developed automated segmentation algorithm. The three dimensional volume rendering of the retina centered on the macular fovea with an image area of 2.5 mm×2.5 mm is shown in FIG. 2a The seven segmented surfaces from the ILM layer to the RPE/ choroid boundary are reconstructed in FIG. 2b so the retina from ILM layer to RPE/Choroid boundary can be divided into six layers, including NFL, GCL+IPL, INL, OPL, ONL+IS and OS. FIG. 2c shows a cross-section image overlaid with the segmented boundaries, and the position of the image is indicated by the planes in FIGS. 2a and 2b. The position of the segmented layers accurately fall on the corresponding boundaries of intra-retinal layers as seen in FIG. 2c, and the six layers of the retina are successfully obtained.

Compared with the two dimensional image segmentation algorithm in retina, the three dimensional expansion dynamic programming method can use the information from neighboring B-scans to improve the accuracy and robustness of the algorithm. Garvin et al. proposed a graph cut-based method for simultaneous segmentation of multiple three dimensional surfaces in retina. However, the computational complexity was significantly increased in the three dimensional data. Compared with the graph cut method, the computational complexity can be significantly reduced by using a dynamic programming method. The processing time for finding an optimal surface from volume data with 400×200×80 voxels was ~0.5 s with parallel techniques in a Quad-Core Intel i7 2.68 GHz workstation. The total processing time for extracting all of the surfaces was ~8 s and the most time-consuming step was the three dimensional median filter processing.

To evaluate the accuracy of the developed automated segmentation algorithm, the results of 27 slides from 3 sets of three dimensional volume data were compared to those achieved by manual segmentation. Nine linear spaced slides (in fast scan plane) from each data set were selected, and the fifth slide was centered at the fovea. The manual boundary detections were obtained by three trained graders using ImageJ software (NIH, Bethesda, Md., USA). The automatic detections were extracted from the corresponding positions of the seven segmented surfaces. The mean±standard deviation of the difference in retinal boundary positions between the automated and manual detections were calculated. The boundaries of retinal layers detected by the automated algorithm were very close to the manual segmentation results in both normal and high myopia eyes. The mean differences were within 2.18 pixels (Table 1) which are similar to two dimensional-based segmentation algorithms. The differences between automatic segmentation and averaged manual segmentation were similar to the difference between manual graders. The layers were segmented based on the normal characteristics of retinal structure. The algorithm may fail with obvious abnormal structures, such as central serous chorioretinopathy (serous detachment of the neurosensory retina), retinitis pigmentosa (disappearance of OS layer). However, the three dimensional expansion dynamic programming method is suitable for interactive segmentation in retinal disease because of significant reduction of computational complexity.

Table 1 shows the differences (mean±SD in pixels) in retinal boundary positions of 27 slides from 3 sets of three dimensional volume data "Between-segmenter" indicates the mean differences of M1 vs M2, M1 vs M3, M2 vs M3. "Auto" indicates the results from automated segmentation. "M1, M2, and M3" indicate the results from three trained graders. "Avg" indicates the averaged results from graders. Each pixel is 2.83 µm.

Figure 3A:
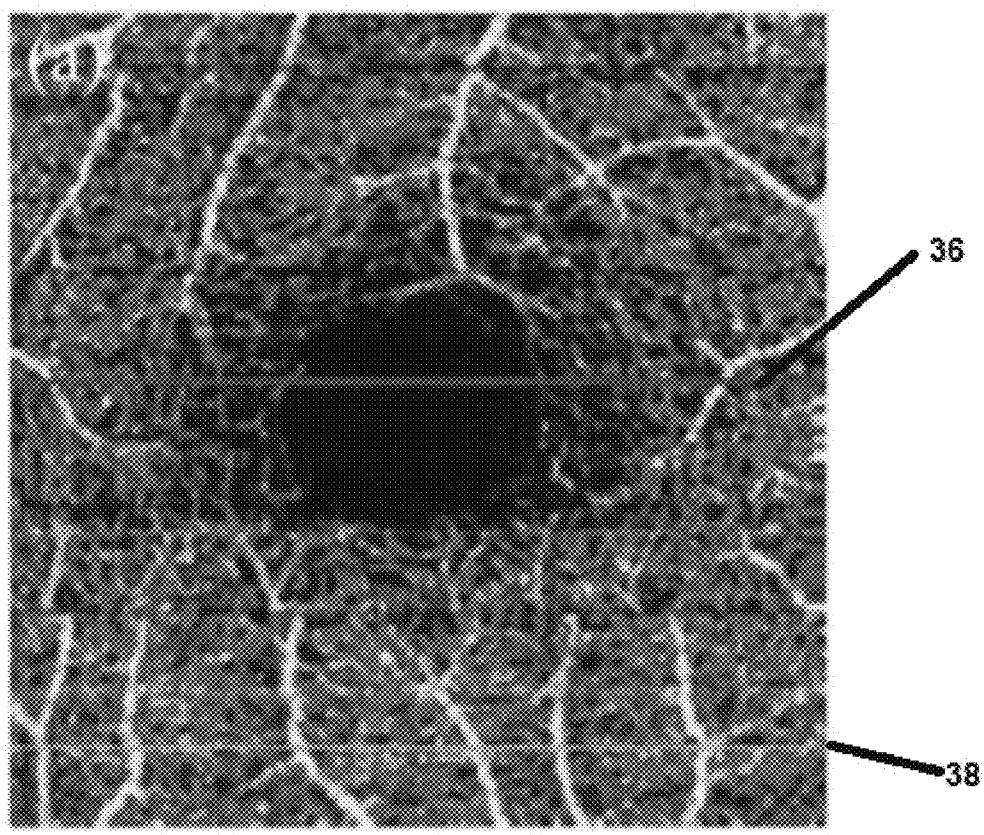
FIG. 3a is an en face maximum intensity projection (MIP) view image of the retinal microvascular network from the ILM layer to the RPE/Choroid boundary.
Figure 3B:
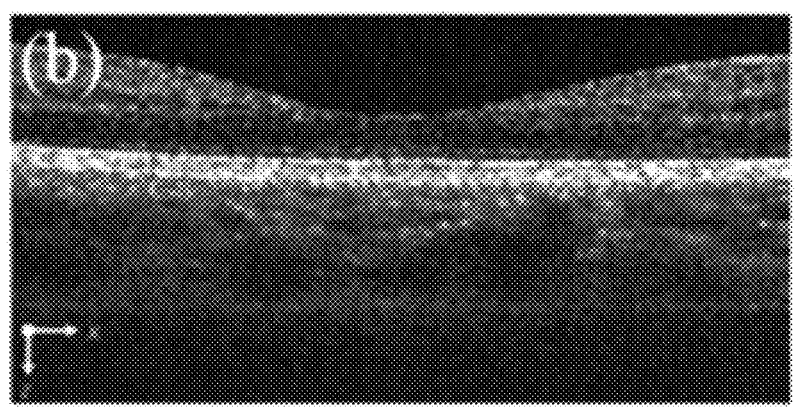
Figure 3C:
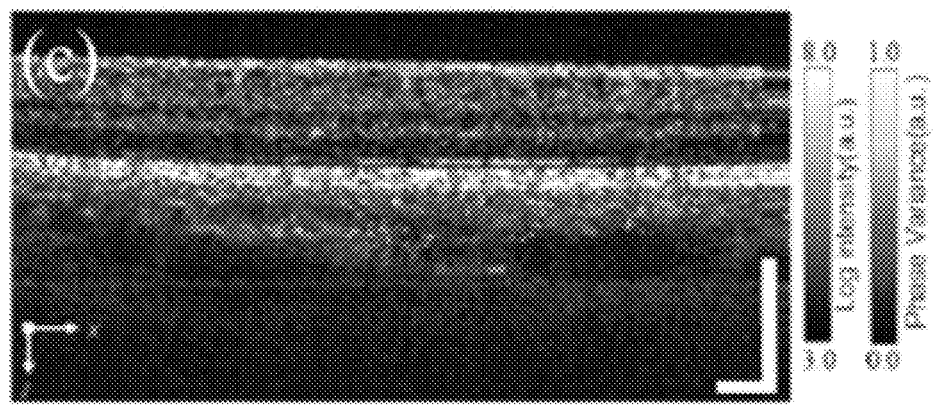

The microvascular network of the macular retina was also obtained by using the IBDV method. FIG. 3a shows en face retina vessels from the HA layer to the RPE/Choroid boundary by using the MIP method. The capillary network can clearly be visualized around the foveal avascular zone. FIGS. 3b and 3c are cross-sectional views of the vessels merged with the intensity images corresponding to the blue line 36 and green line 38 in FIG. 3a respectively. Most of the vessel signals are located in the inner retina and choroid. There are also some Doppler variance signals in the outer retina which should be avascular. This should relate to the shadow artifact from the upper layers. Total processing for getting the IBDV images from the raw data set is ~30 s after accelerated by GPU (NVIDIA, GeForce GTX 460).

Figure 4A:
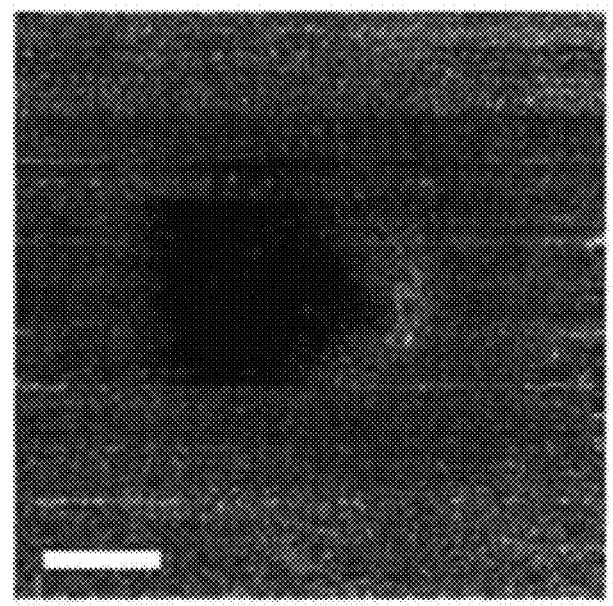
FIG. 4a is an en face MIP view microvascular image of the NFL layer obtained by the intensity-based Doppler variance method combined with three dimensional segmentation of the retina.
Figure 4B:
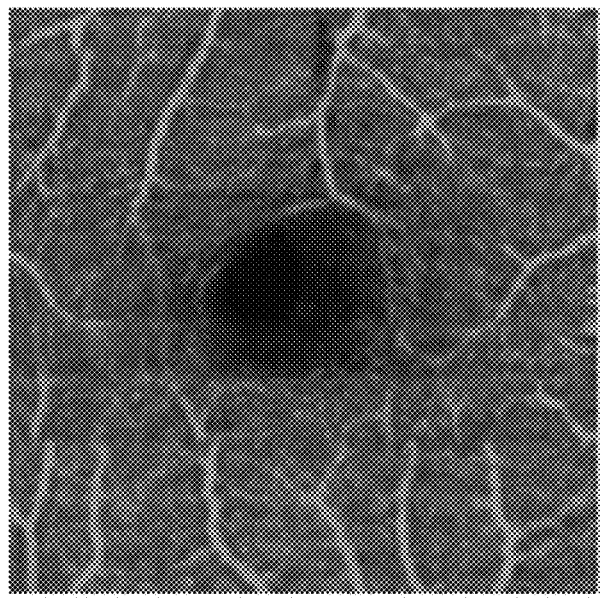
FIG. 4b is an en face MIP view microvascular image of the GCL+IPL layer obtained by the intensity-based Doppler variance method combined with three dimensional segmentation of the retina.
Figure 4C:
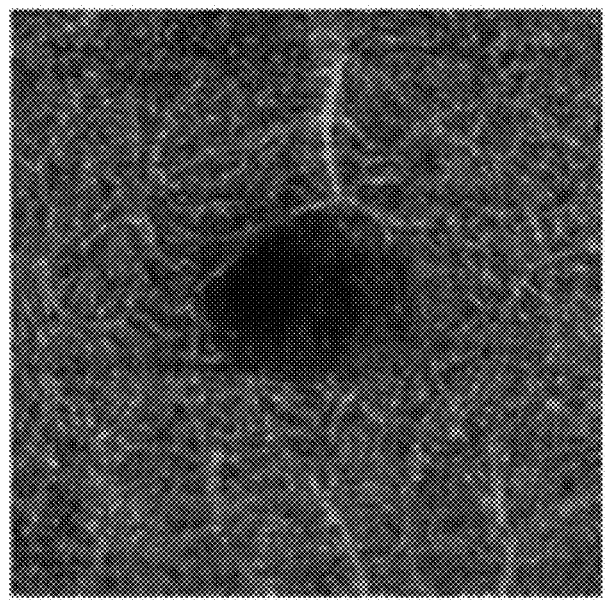
FIG. 4c is an en face MIP view microvascular image of the INL layer obtained by the intensity-based Doppler variance method combined with three dimensional segmentation of the retina.
Figure 4D:
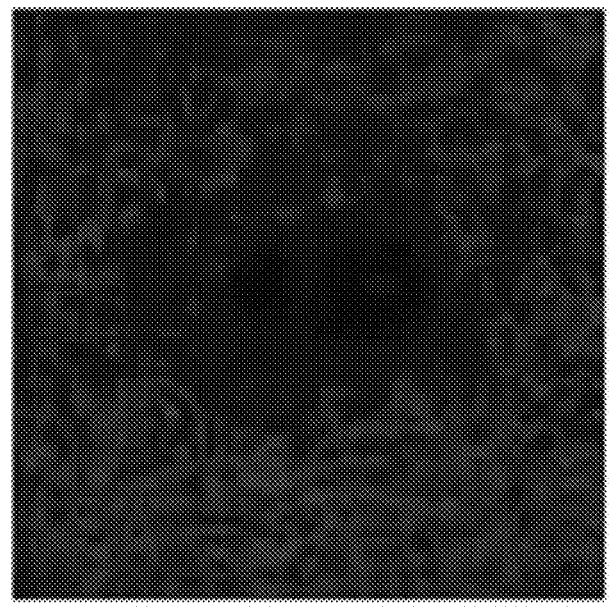
FIG. 4d is an en face MIP view microvascular image of the OPL layer obtained by the intensity-based Doppler variance method combined with three dimensional segmentation of the retina.
Figure 4E:
FIG. 4e is an en face MIP view microvascular image of the ONL+IS layer obtained by the intensity-based Doppler variance method combined with three dimensional segmentation of the retina.
Figure 4F:
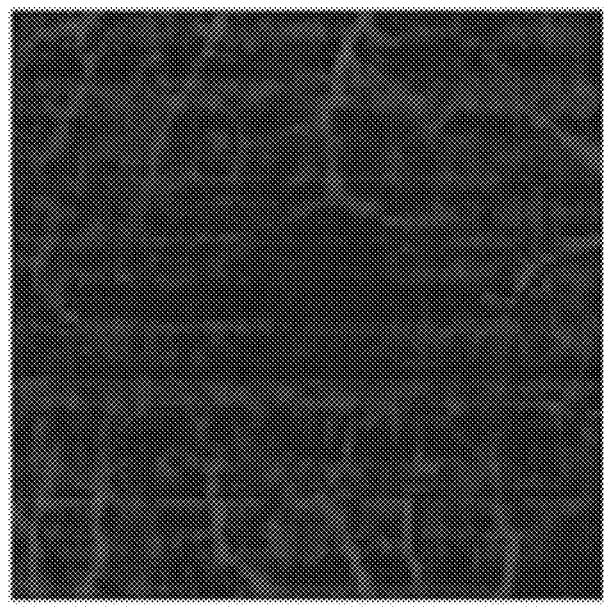
FIG. 4*f* is an en face MIP view microvascular image of the OS+RPE layer obtained by the intensity-based Doppler variance method combined with three dimensional segmentation of the retina.
Figure 4G:
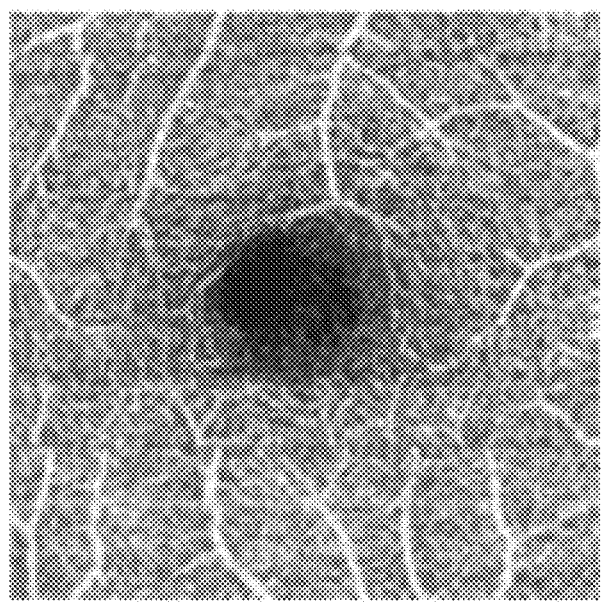
FIG. 4*g* is an en face MIP view microvascular image of the MIP layer obtained by the intensity-based Doppler variance method combined with three dimensional segmentation of the retina.
Figure 4H:
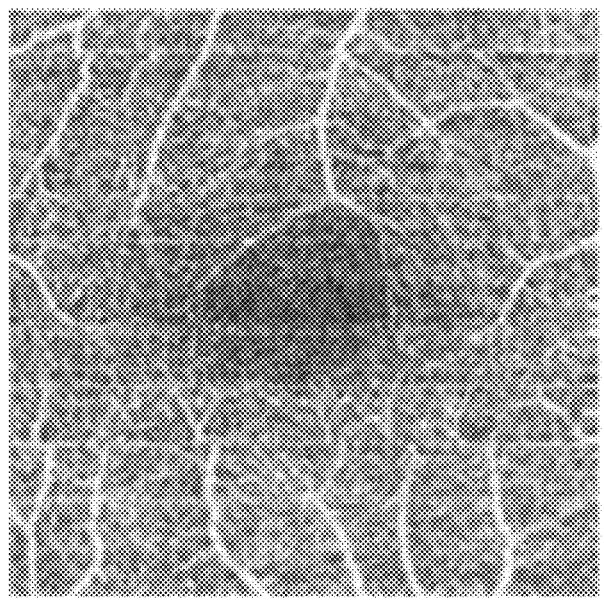
FIG. 4*h* is an en face MIP view microvascular image of the total retina from the NFL/GCL boundary to the OPL/ONL boundary obtained by the intensity-based Doppler variance method combined with three dimensional segmentation of the retina.
Figure 4I:
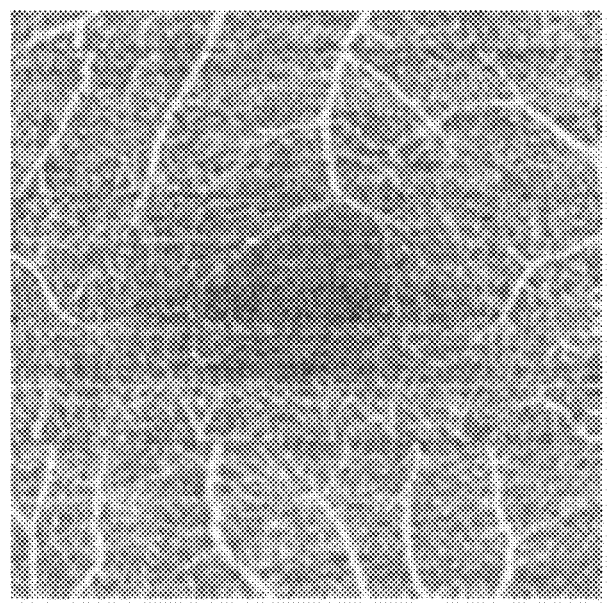
FIG. 4*i* is an en face MIP view microvascular image of the retina with a range 400 µm depth above the RPE/Choroid boundary obtained by the intensity-based Doppler variance method combined with three dimensional segmentation of the retina.

Combined with seven surfaces of the intraretinal data, the microvascular network of the macular retina can be divided into six layers, FIGS. 4a-f present an en face MIP microvascular view of the six layers, including NFL, GCL+IPL, INL, OPL ONL+IS, OS+RPE respectively. Most of the vessels in the macular region are located in the inner retina, which agree with the known anatomy. In FIGS. 4h and 4i, some deeper microvessels may be sheltered from upper vessels in the en face view of the total retina. Segmentation of the individual layers can help to separate these vessels. Microvascular images of individual layers may provide some essential information for early diagnosis of some retinal diseases. The shadow artifacts are also observed in the MIP view of the individual layers as best seen in FIG. 4f. However, most of the shadow artifacts are generated from the relatively large vessels as seen in FIGS. 3b and 3c Compared with simply projecting the maximum values with a range of 400 um depth above the RPE/Choroid boundary seen in FIG. 4i, the MIP view from ILM layer to RPE/Choroid boundary (FIG. 4h) can help to improve the quality of an OCT angiography image. Because the retinal vessels are concentrated in the inner retinal layers (GCL, IPL, INL, OPL), the contrast of the microvascular images can be improved by projecting the maximum values from the NFL/GCL boundary to the OPL/ONL boundary seen in FIG. 4g rather than the total retina as seen in FIG. 4h.

In summary, we have demonstrated a three dimensional segmentation method with IBDV based on SS-OCT with a center wavelength of 1050 nm. The feasibility of the method was tested on three dimensional data of a retina centered on the macular fovea with an image area of 2.5 mm×2.5 mm. The seven surfaces of the intra-retinal layers were successfully segmented automatically by using a three dimensional

TABLE 1

| Retinal Layer | Between-segmenter | Auto vs M1 | Auto vs M2 | Auto vs M3 | Auto vs Avg |
|---|---|---|---|---|---|
| ILM | 0.89 ± 0.80 | 1.25 ± 1.10 | 1.44 ± 1.14 | 1.61 ± 1.15 | 1.38 ± 1.03 |
| NFL/GCL | 1.15 ± 1.03 | 1.51 ± 1.21 | 1.64 ± 1.39 | 1.79 ± 1.40 | 1.52 ± 1.22 |
| IPL/INL | 1.81 ± 1.72 | 1.87 ± 1.41 | 2.18 ± 1.60 | 1.74 ± 2.01 | 1.66 ± 1.33 |
| INL/OPL | 1.55 ± 1.35 | 1.91 ± 1.34 | 1.55 ± 1.31 | 2.03 ± 1.69 | 1.56 ± 1.36 |
| OPL/ONL | 1.57 ± 1.68 | 1.60 ± 1.39 | 1.68 ± 1.48 | 1.93 ± 2.10 | 1.55 ± 1.34 |
| IS/OS | 0.80 ± 0.73 | 1.04 ± 0.89 | 1.28 ± 0.93 | 1.40 ± 0.98 | 1.16 ± 0.86 |
| RPE/Choroid | 1.15 ± 1.03 | 1.70 ± 1.32 | 1.72 ± 1.24 | 1.69 ± 1.18 | 1.59 ± 1.10 | expansion of a dynamic programming method. The IBDV method was used to acquire the microvascular network of the macular retina. The en face MIP microvascular network images of six layers were obtained after combining the three dimensional surfaces of the segmented layers. The morphology of the microvascular network for the individual intraretinal layers can be visualized, and the segmentation method can also be used to enhance the contrast of the vascular images. This method has potential for earlier diagnosis and precise monitoring in retinal vascular diseases.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are et forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A method for microvascular imaging comprising:
   scanning a target tissue having a microvascular network using intensity-based Doppler variance optical coherence tomography (IBDV OCT) with a swept source to obtain three dimensional optical coherence tomography (OCT) data of the target tissue;
   preprocessing the OCT data;
   determining boundaries of tissue layers within the target tissue, the boundaries being determined by searching for an optimal path; and
   displaying selected microvascular image views of the three dimensional OCT data of the target tissue with the determined boundaries of the tissue layers within the target tissue,
   where the target tissue is the retina and where determining boundaries of tissue layers within the target tissue comprises determining an initial location of the ILM and RPE layers from an A-scan profile,
   where the determining an initial location of the ILM and RPE layers from an A-scan profile then further comprises smoothing the ILM/RPE layers using a polynomial method, limiting a search area for the ILM layer based on the initial ILM boundary and refining the location of the layer by finding the optimal path in the limited search area to determine retina location, and
   where determining boundaries of tissue layers within the target tissue comprises determining limited search areas for other boundaries of tissue layer based on the characteristics of retinal structure by first determining the outer plexiform layer/outer nuclear layer (OPL/ONL layer) boundary and photoreceptor inner segment layer/outer segment (IS/OS) layer boundary by using an intensity transition along a z axis direction between adjacent layers being in opposite directions, surfaces of the ILM layer, nerve fiber layer/retinal ganglion layer (NFL/GCL) boundary, inner plexiform layer/inner nuclear layer (IPL/INL) boundary, INL/OPL boundary, OPL/ONL boundary, IS/OS boundary, and RPE/Choroid boundary being determined by limiting a search region corresponding to the layer based on previous layers.

2. The method of claim 1 where scanning a target tissue having a microvascular network using intensity-based Doppler variance optical coherence tomography with a swept source to obtain three dimensional OCT data of the target tissue comprises making repeated scans at each position to achieve maximized time differences to improve sensitivity.

3. The method of claim 1 where preprocessing the OCT data comprises preprocessing the OCT data with a subpixel registration algorithm to reduce the eye movement.

4. The method of claim 1 where preprocessing the OCT data comprises preprocessing the OCT data with a graphics processing unit (GPU) to accelerate data processing to achieve real-time preview of the acquired OCT data.

5. The method of claim 4 where preprocessing the OCT data with a graphics processing unit (GPU) to accelerate data processing to achieve real-time preview of the acquired OCT data comprises performing fixed pattern noise removal, spectral shaping, zero-padding and numerical dispersion compensation accelerated by GPU processing.

6. The method of claim 1 where preprocessing the OCT data comprises preprocessing the OCT data with a threshold based on the histogram analysis of the averaged intensity images to remove noise.

7. The method of claim 1 where determining boundaries of tissue layers within the target tissue comprises applying a two dimensional average filter to the segmentation results to get smooth surfaces for the corresponding boundaries.

8. The method of claim 1 where displaying selected microvascular image views of the three dimensional data of the target tissue with the determined boundaries of the tissue layers within the target tissue comprises combining volumetric microvascular signal of the retina with three dimensional surface data of the boundaries by segmenting IBDV OCT data into different layers.

9. The method of claim 8 further comprising producing an en face projection view of the microvascular network for intra-retinal layers by using maximum intensity projection (MIP).

10. The method of claim 1 where determining boundaries of tissue layers within the target tissue, the boundaries being determined by searching for an optimal path, comprises transforming detection of the boundaries into an optimization problem that searches for an optimal path across the boundaries.

11. The method of claim 10 where transforming detection of the boundaries into an optimization problem that searches for an optimal path across the boundaries comprises:
treating each pixel as a node in a graph with links connecting the nodes;
assigning weights to the links based on the intensity of the pixels;
defining a virtual start node which connects to nodes in a first column in a two dimensional image grid with the corresponding weights of the links connected to the start node being assigned to zero;
defining a virtual end node which connects to nodes in a last column of the two dimensional image grid;
defining a boundary by searching for a minimum cost of a path from the start node to end node; and
defining the boundary surfaces by sequentially searching in a fast scan plane and then in a slow scan plane for three dimensional expansion.

12. The method of claim 11 where defining a boundary by searching for a minimum cost of a path from the start node to end node comprises:
using an iterative cost function in two directions in a volumetric image $R(x, y, z)$ of size $X \times Y \times Z$;
where the volumetric image $R(x, y, z)$ is an intensity gradient image along a vertical direction which is obtained by a dark-to-light or light-to-dark intensity transition;
where the X and Y are the numbers of fast scan and slow scan respectively, and Z denotes the depth;
where the iterative cost function is given by $$C_1(x, y, z) = \min_{-d_1 \le i \le d_1} \{C_1(x+i, y-1, z) + \alpha_1|i| + w(x+i, x)\} \quad (2)$$
$$C_2(x, y, z) = \min_{-d_2 \le j \le d_2} \{C_2(x-1, y+j, z) + \alpha_2|j|\} + C_1(x, y, z)$$

for $1 < x \le X$ and $1 < y \le Y$;
where $C_1$ and $C_2$ are the accumulation costs in the x–z plane and the y–z plane, respectively;
where in initialization of $C_1$ and $C_2$ are assigned by $R(x, y, z)$;
where the parameters $d_1$ and $d_2$ constrain a searching range used to control the smoothness of boundary surfaces;
where the parameters $\alpha_1$ and $\alpha_2$ are used to control the smoothness of the surfaces;
where $w(x+i, x)$ denotes the weights from node $(x+i, y-1, z)$ to node $(x, y, z)$ and the weights are calculated as follows:

$$w(x+i,x)=2-r(x+i,y-1,z)-r(x,y,z)+w_{min} \quad (3)$$

where $r(x, y, z)$ is the gradient value of the node $(x, y, z)$ which is normalized to values between 0 and 1;
where the $w_{min}$ is a minimum weight for system stabilization.

13. The method of claim 12 where for retinal segmentation, the parameters $\alpha_1$ and $\alpha_2$ are set to zero.

14. The method of claim 1 where determining boundaries of tissue layers within the target tissue, the boundaries being determined by searching for an optimal path comprises automatically determining boundaries of tissue layers within the target tissue, the boundaries being determined by searching for an optimal path.

15. A method for imaging a plurality of layer segments in retinal tissue characterized by a plurality of surfaces of corresponding intra-retinal layers comprising:
imaging the plurality of layer segments in retinal tissue using intensity-based Doppler variance (IBDV) OCT based on swept-source OCT; and
using three dimensional segmentation of the intensity-based Doppler variance (IBDV) OCT data image of the plurality of layer segments in retinal tissue to determine a three dimensional shape of each of the plurality of surfaces of intra-retinal layers using automated boundary detection, where corresponding boundaries of the plurality of surfaces of intra-retinal layers are obtained by searching for an optimal path across the boundaries, where searching for an optimal path across the boundaries comprises:
treating each pixel as a node in a graph with links connecting the nodes;
assigning weights to the links based on the intensity of the pixels;
defining a virtual start node which connects to nodes in a first column in a two dimensional image grid with the corresponding weights of the links connected to the start node being assigned to zero;
defining a virtual end node which connects to nodes in a last column of the two dimensional image grid;
defining a boundary by searching for a minimum cost of a path from the start node to end node; and
defining the boundary surfaces by sequentially searching in a fast scan plane and then in a slow scan plane for three dimensional expansion.

16. The method of claim 15 where imaging the plurality of layer segments in retinal tissue using intensity-based Doppler variance (IBDV) OCT based on swept-source OCT comprises obtaining complex valued OCT image data using a three dimensional raster scan and preprocessing the OCT image data by using a plurality of sequential scans at each position, by averaging intensity image data, by using a threshold based on histogram analysis of the averaged intensity image data to remove the noise, by using a subpixel registration algorithm to reduce eye movement, and by using GPU data processing to achieve real-time preview of the acquired data.

\* \* \* \* \*